United States Patent [19]

Olson

[11] Patent Number: 5,499,970
[45] Date of Patent: Mar. 19, 1996

[54] DEBRIDEMENT TIP

[75] Inventor: Daniel H. Olson, Louisville, Ohio

[73] Assignee: Zimmer, Inc., Warsaw, Ind.

[21] Appl. No.: 294,690

[22] Filed: Aug. 23, 1994

[51] Int. Cl.$^6$ ................................................ A61M 1/00
[52] U.S. Cl. ............................ 604/35; 604/27; 604/43;
604/73; 604/264
[58] Field of Search ............................ 604/35, 39–43,
604/73–76, 264, 275, 27

[56] References Cited

U.S. PATENT DOCUMENTS

| | | | |
|---|---|---|---|
| 695,470 | 3/1902 | Milam | 604/42 |
| 701,124 | 5/1902 | Allen | 604/41 |
| 805,826 | 11/1905 | Vidaver | 604/39 |
| 4,886,492 | 12/1989 | Brooke | 604/49 |
| 5,076,787 | 12/1991 | Overmyer | 433/95 |

FOREIGN PATENT DOCUMENTS

| | | | |
|---|---|---|---|
| 0565345 | 11/1932 | Germany | 604/39 |

*Primary Examiner*—John D. Yasko
*Assistant Examiner*—Laird J. Knights
*Attorney, Agent, or Firm*—Cary R. Reeves

[57] ABSTRACT

The debridement tip of the instant invention provides efficient cleaning action and is capable of handling excessive amounts of debris. It also is able to track irregular debridement sites such as canals and gutter wounds. It furthermore visually indicates when it is clogged. The debridement tip comprises an inner cannula and an outer cannula. The outer cannula is flexible so that it tracks the debridement site. The outer cannula surrounds the inner cannula and forms an enlarged collection chamber near a proximal end of the debridement tip for collecting debris. The collection chamber is easily opened to allow removal of the debris. The collection chamber is also flexible so that if the tip becomes clogged either the outer cannula or the collection chamber or both will collapse thus visually indicating the clogged condition. A filter at one end of the collection chamber prevents large debris from leaving the chamber. The filter is shaped to resist clogging. A suction chamber behind the filter ensures suction across the full diameter of the filter to further resist clogging. The distal end of the outer cannula is collapsible to a smaller diameter so that it can extend into narrow passages.

15 Claims, 4 Drawing Sheets

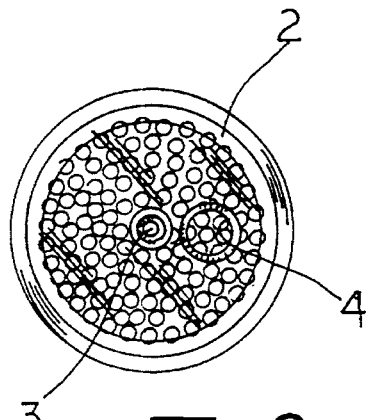
Fig. 2
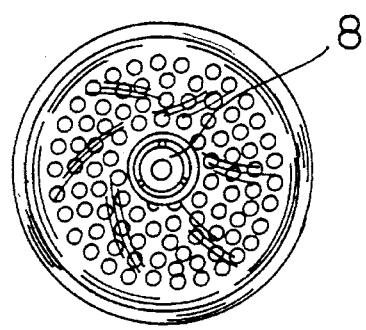
Fig. 3
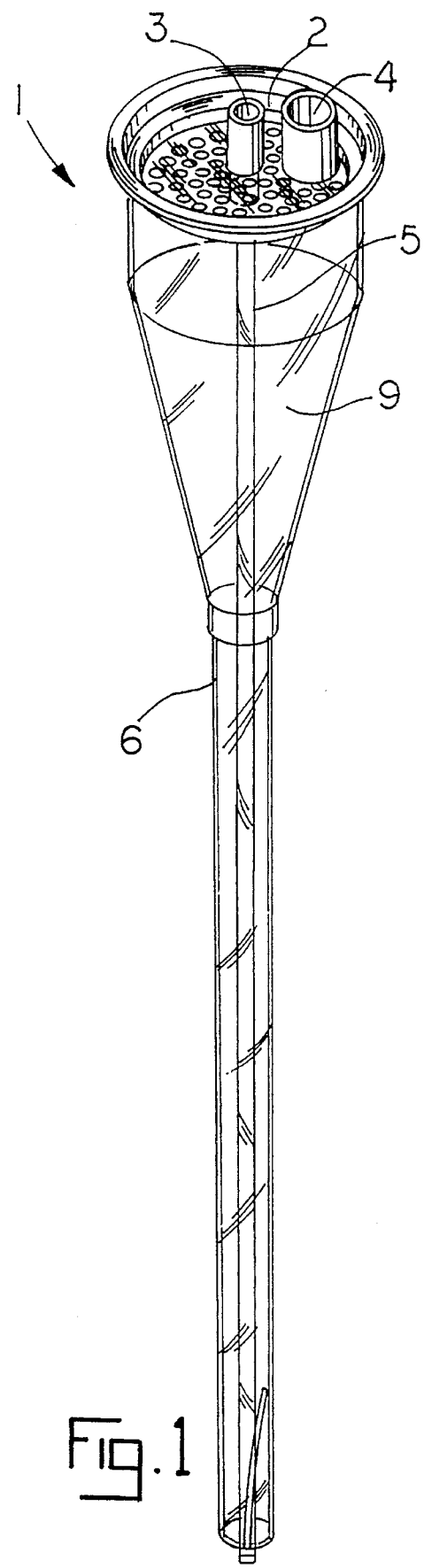
Fig. 9
Fig. 1

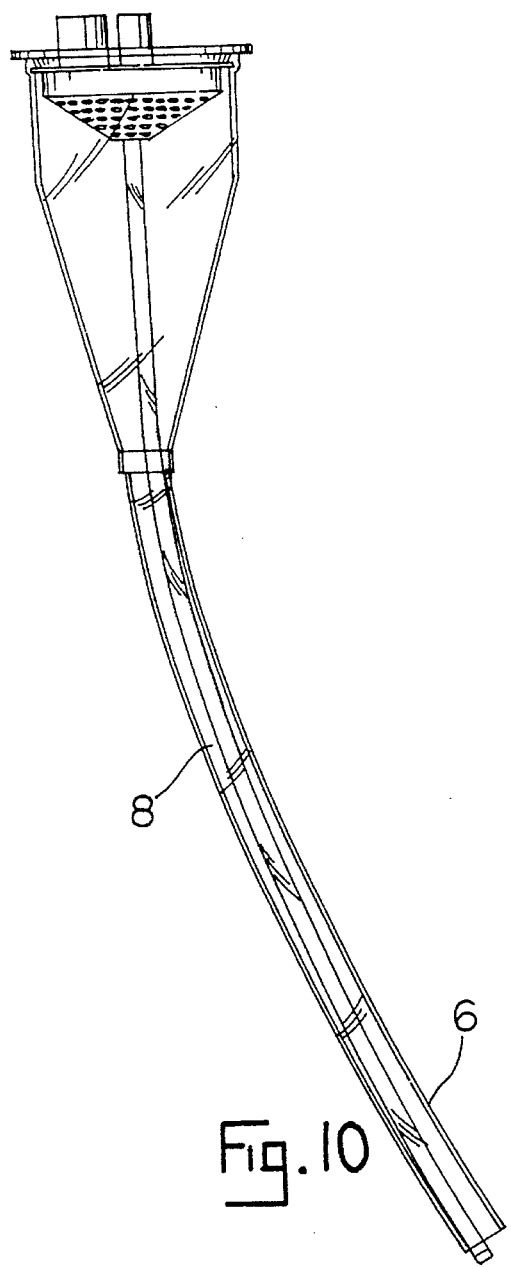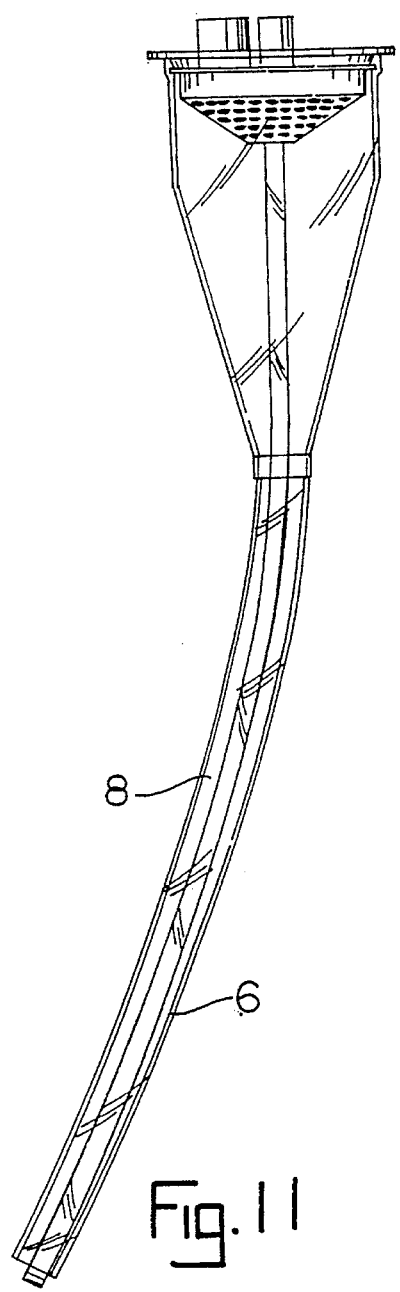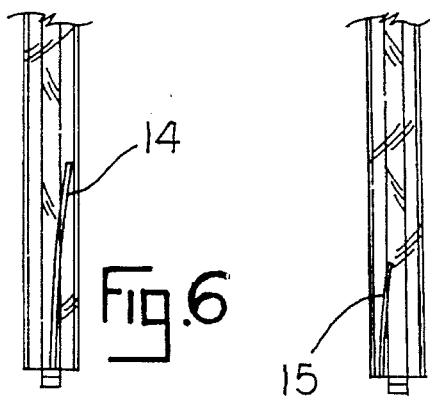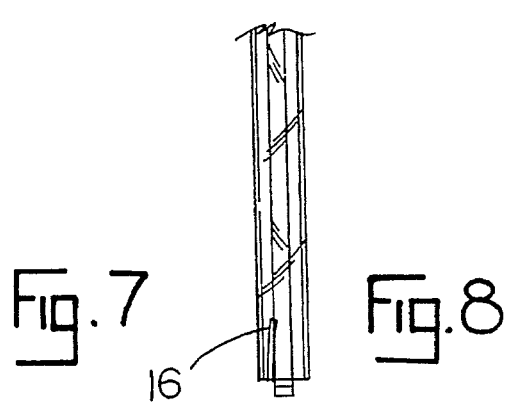

DEBRIDEMENT TIP

BACKGROUND OF THE INVENTION

The present invention relates to a debridement tip for irrigating and suctioning a wound or surgical site. More specifically, it relates to an improved debridement tip able to handle large amounts of debris without clogging and able to flexibly extend deep into the debridement site.

Debridement tips are widely used in surgical procedures and wound management to clean body tissues and are especially useful in orthopaedic cases. Debridement tips are most challenged when there is a large amount of debris to be suctioned away such as in hip revision surgery or in procedures that involve reaming or milling large quantities of bone or removing loose necrotic tissue. Prior tips clog quickly when presented with this type of debris. Some prior patents that teach using a filter in a suction tip include U.S. Pat. Nos. 5,078,603; 5,076,787; 4,886,492; and 4,468,217.

U.S. Pat. No. 4,692,140 while not teaching the use of a filter, discloses an efficient debridement system comprising an inner cannula and an outer cannula. The inner cannula delivers irrigating fluid to the surgical site while the outer cannula simultaneously removes excess fluid and debris with suction.

Prior suction tips and debridement systems are typically constructed of rigid materials such as styrene, acrylic, polycarbonate, or other materials with a high durometer hardness, for example 98 Shore A or above. These prior tips are made rigid in part to prevent them from collapsing under high suction, especially when they become clogged. For this reason, if a rigid tip becomes clogged there is no readily apparent indication of the clogged condition. Furthermore, rigid tips are difficult to use in irregular canals, furrows, gutter wounds and trauma punctures because they do not bend to follow the wound.

SUMMARY OF THE INVENTION

The debridement tip of the instant invention provides efficient cleaning action and is capable of handling excessive amounts of debris. It also is able to track irregular debridement sites such as canals and gutter wounds. It furthermore visually indicates when it is clogged. The debridement tip comprises an inner cannula and an outer cannula. The outer cannula is flexible so that it tracks the debridement site. The outer cannula surrounds the inner cannula and forms an enlarged collection chamber near a proximal end of the debridement tip for collecting debris. The collection chamber is easily opened to allow removal of the debris. This is useful for restoring suction to the debridement tip as well as for collecting debris for analysis or grafting. The collection chamber is flexible so that if the tip becomes clogged the collection chamber will collapse and thus visually indicate the clogged condition. A filter at one end of the collection chamber prevents the debris from leaving the chamber. The filter is shaped to resist clogging. A suction chamber behind the filter ensures suction across the full diameter of the filter to further prevent clogging. The distal end of the outer cannula is collapsible so that it can extend into narrow passages.

BRIEF DESCRIPTION OF THE DRAWINGS

FIG. 1 is a perspective view of the debridement tip of the present invention.

FIG. 2 is a top plan view of the debridement tip of the present invention.

FIG. 3 is a bottom plan view of the debridement tip of the present invention.

FIG. 6 is a side view of the distal end of the debridement tip of the present invention.

FIG. 7 is a side view of the distal end of the debridement tip of the present invention rotated 120 degrees from FIG. 6.

FIG. 8 is a side view of the distal end of the debridement tip of the present invention rotated 120 degrees from FIG. 7.

FIG. 9 is a bottom plan view of just the distal end of the debridement tip of the present invention showing the distal end collapsed to a smaller diameter.

FIG. 10 is a side view of the debridement tip of the present invention showing the outer cannula flexed to change the shape of the suction path.

FIG. 11 is a side view of the debridement tip of the present invention showing the outer cannula flexed to change the shape of the suction path.

DETAILED DESCRIPTION OF THE INVENTION

Figure 4:
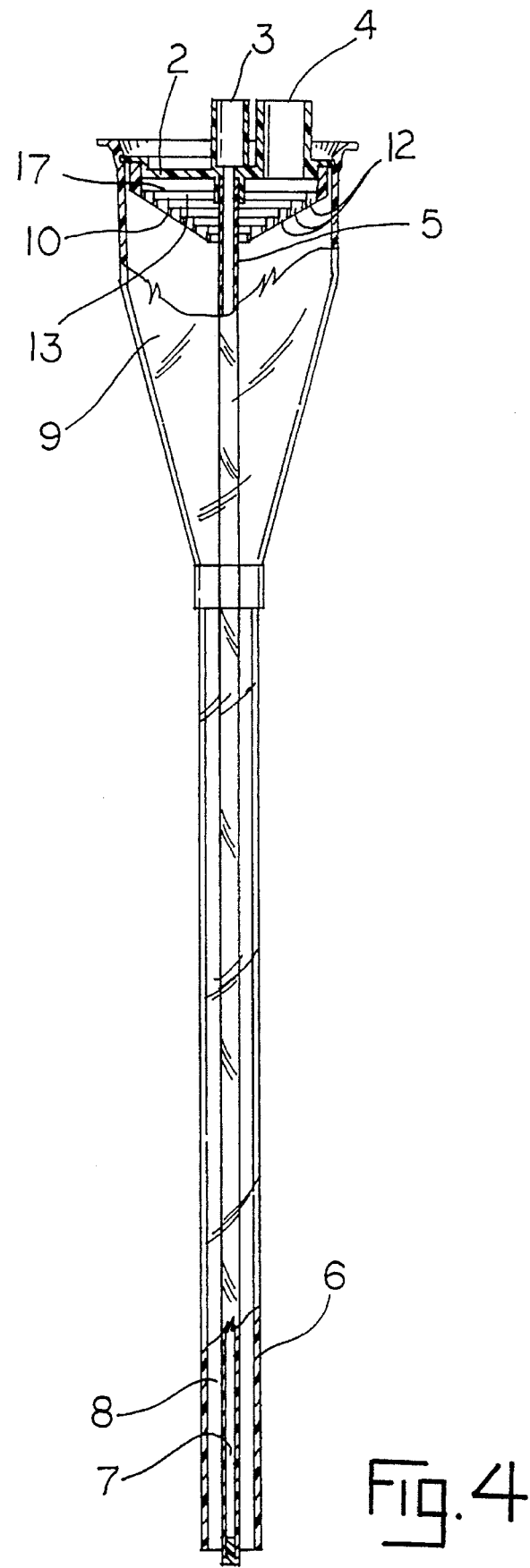
FIG. 4 is a partial side sectional view of the debridement tip of the present invention.
Figure 5:
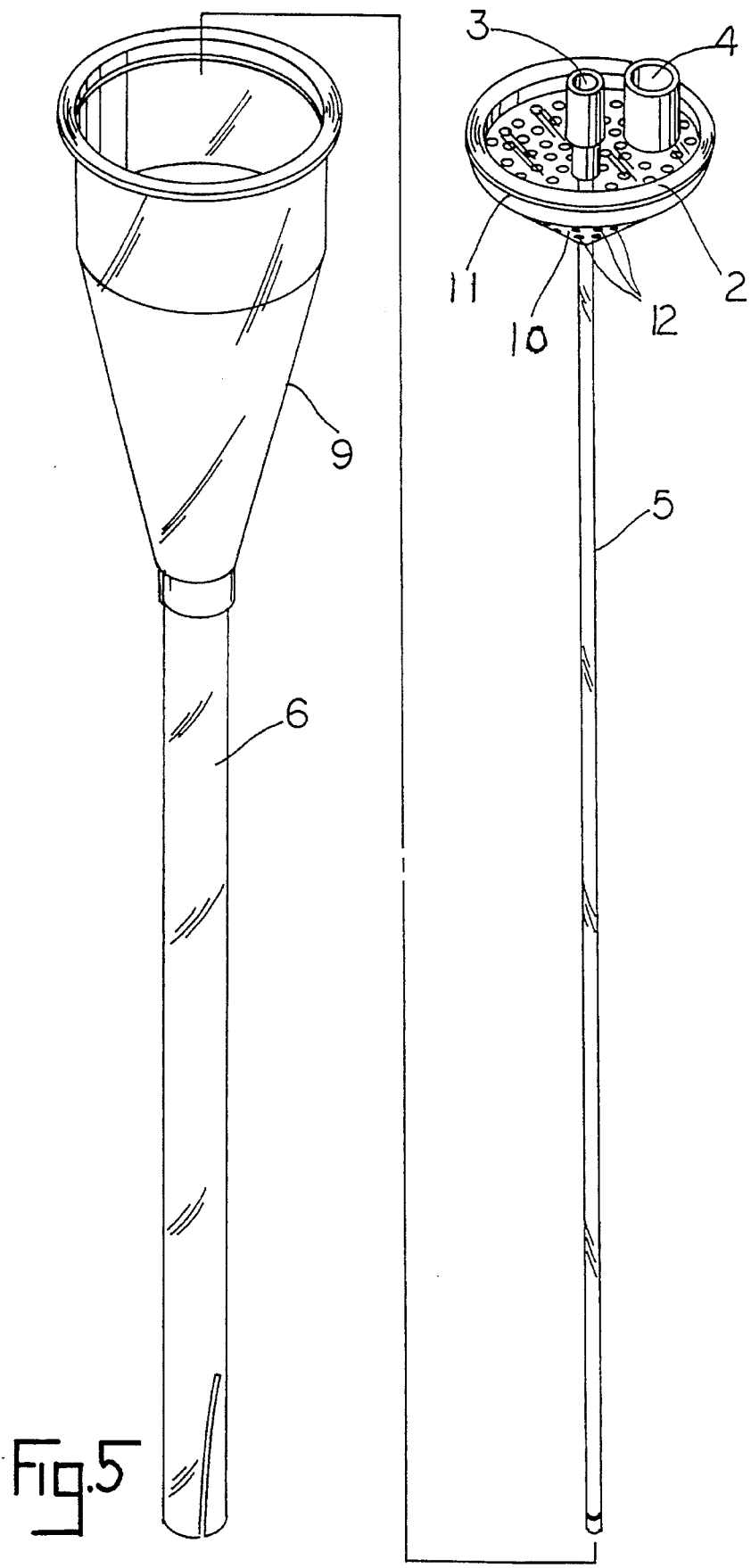
FIG. 5 is a perspective view of the debridement tip of the present invention showing the tip disassembled for cleaning.

Referring to FIGS. 1 through 5, a debridement tip 1 has a proximal end for attachment to a source of irrigation fluid and to a suction source and a distal end for debriding a surgical site. A base 2 is adjacent the proximal end and contains a fluid port 3 and a suction port 4. An inner cannula 5 is attached to the base 2 in fluid communication with the fluid port. The inner cannula 5 defines a fluid path 7 from the proximal end to the distal end of the debridement tip 1. An outer cannula 6 is attached to the base 2 in fluid communication with the suction port 4. The outer cannula 6 surrounds the inner cannula 5 thus defining an annular suction path 8 from the distal end to the proximal end of the debridement tip 1. Preferably, the outer cannula 6 is flexible to permit it to track irregular debridement sites such as curving canals or gutter wounds. Flexibility of the outer cannula 6 also allows it to be manipulated by the user to dislodge debris trapped in the annular suction path 8. Bending the outer cannula 6 back and forth into a curve as shown in FIGS. 10 and 11 is effective to change the shape of the annular suction path 8 and dislodge debris. Materials with a durometer hardness in the range of 5 to 90 Shore A allow for efficient tracking and unclogging. More preferably the durometer hardness is in the range of 65 to 90 Shore A. A change in durometer hardness from 98 Shore A to 90 Shore A results in a significant change in flexibility of the outer cannula 6. While prior suction tips are rigid to prevent collapse, the debridement tip of the present invention may collapse, at least partially, when it becomes plugged thus positively indicating the clogged condition.

A collection chamber 9 comprises an enlargement of the outer cannula 6 near the proximal end. The collection chamber 9 forms an enlarged portion of the annular suction path 8. Preferably the collection chamber 9 is a frustoconical shape increasing from a diameter equal to the distal diameter of the outer cannula 6 to a diameter equal to two to ten times the distal diameter of the outer cannula 6, more preferably equal to four to seven times the distal diameter of the outer cannula. The collection chamber 6 increases in diameter in the direction of flow of fluid and debris through the collection chamber 6. Preferably the collection chamber 6 expands from its minimum diameter to its maximum diameter over a distance equal to two to twelve times the distal diameter of the outer cannula, more preferably five to 9 times the distal diameter of the outer cannula. The size of the collection chamber 9 enables it to contain large amounts of debris. The frustoconical shape of the collection chamber 9 prevents stagnant areas from forming within the collection chamber 9. As fluid is drawn into the collection chamber 9, the debris in the chamber is churned and kept in motion so that fluid and small debris particles can pass by the larger debris particles rather than compacting into an immovable plug. The churning action thereby increases the longevity of the tip between cleanings. Preferably, the collection chamber 9 is also made of a flexible material having a durometer hardness in the range of 5 to 90 Shore A, more preferably in the range of 65 to 90 Shore A. This flexibility allows the collection chamber 9 to collapse, at least partially, when the suction path 8 becomes clogged. Collapse of the collection chamber 9 is a positive visual indicator of a clogged condition. A collection chamber made of polyvinylchloride having a wall thickness of approximately 0.060 inches and a durometer hardness of 82 Shore A was tested. The collection chamber had a 0.5 inch minimum outside diameter and a 2.5 inch maximum outside diameter yielding a maximum diameter to minimum diameter ratio of 5. The collection chamber expanded from its minimum diameter to its maximum diameter over a 3 inch long span yielding a length to expand from minimum to maximum diameter equal to six times the minimum diameter. This collection chamber was found to have adequate capacity for typical surgical procedures. When the outer cannula was completely blocked, the collection chamber began to visually collapse between 130 and 170 mmHg at room temperature.

In the preferred embodiment, a filter 10 is located in the suction path 8 near the proximal end of the debridement tip. The filter 10 is preferably a frustoconical projection. The larger end of the filter 10 is attached to the base 2 with the perimeter of the filter adjacent the perimeter 11 of the base. The filter 10 decreases in diameter as it extends into the collection chamber. The inner cannula 5 preferably extends through the middle of the filter 10 so that the filter 10, inner cannula 5, and outer cannula 6 are coaxial and symmetrical. The filter 10 contains a plurality of holes 12 to allow fluid and small debris particles to pass to the suction port 4 and to retain large debris particles in the collection chamber 9. Furthermore, it is preferable for the filter 10 and base 2 to enclose a post-filter suction chamber 13. This suction chamber is in fluid communication with the holes 12 in the filter and in fluid communication with the suction port 4. In this way, suction is distributed across the backside of the filter 10 to all of the filter holes 12. The filter 10 preferably includes annular ribs 17 to strengthen the filter. Finally, the filter 10 is preferably securely attached to the base 2 and the outer cannula 6 and collection chamber are attached to the base 2 by a snap fit between the base 2 and the collection chamber 9 so that the outer cannula 6 and collection chamber 9 can be detached from the base 2 for emptying and cleaning.

The outer cannula 6 preferably is collapsible at the distal end. Collapsibility is provided by a slit in the outer cannula. Preferably, the outer tube contains three longitudinal slits 14, 15, and 16 of unequal length, as shown in FIGS. 6 through 8. These slits form segments which can overlap one another and collapse to a smaller diameter, as shown in FIG. 9, to allow the outer cannula 6 to extend into a narrow passage.

In use, the debridement tip 1 is assembled as shown in FIG. 1. The fluid port 3 and the suction port 4 are connected to fluid and suction sources respectively. The distal end of the debridement tip 1 is applied to the debridement site. For example, it is extended into a femoral canal in hip revision surgery or a tunneled gutter wound. The fluid discharged from the inner cannula 5 helps to dislodge bone, cement, fat, necrotic tissue or other debris from the debridement site. Simultaneously, the outer cannula 6 suctions the debris and irrigation fluid out of the debridement site. As the debris travels along the suction path 8 it enters the collection chamber 9. If the suction path 8 becomes clogged, the outer cannula 6 or the collection chamber 9 or both will collapse, at least partially, thus indicating the clogged condition. The flexible outer cannula 6 can be manipulated to change the shape of the suction path 8 and thus release the clogging debris.

The collection chamber 9 contains a large amount of debris without clogging. Furthermore, the frustoconical shape of the collection chamber results in churning of the debris thus preventing it from compacting and plugging the suction path. The filter 10 prevents debris larger than the filter holes 12 from reaching the suction port 4. The post-filter suction chamber 13 ensures that suction is distributed to all of the filter holes 12 so that if some become clogged the debridement tip will continue to function. If the collection chamber 9 becomes full, it can be snapped off of the base 2, emptied, and snapped back on to resume debridement. Bone and other tissues collected in the collection chamber 9 can also be used for laboratory testing and for grafting purposes.

As the debridement tip 1 is pushed deeper into the debridement site, the distal end of the outer cannula 6 can collapse to a narrower diameter to allow it to enter narrow passages and the flexible tip will track irregularly shaped wounds. In this way the tip is able to remove all of the fluid and debris from the debridement site.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A debridement tip having a proximal end and a distal end, the proximal end having connectors for connecting to an irrigation source and a suction source, the tip comprising:

a base adjacent the proximal end, the base containing a fluid port and a suction port, an inner cannula attached to the base in communication with the fluid port and defining a fluid path from the proximal end to the distal end;

an outer cannula surrounding the inner cannula, the outer cannula attached to the base in communication with the suction port and defining an annular suction path from the distal end to the proximal end, the paths defined by the inner and outer cannulas being two separate paths extending between the proximal and distal ends of the debridement tip so that fluid is simultaneously discharged from the inner cannula at the distal end of the debridement tip and sucked into the outer cannula at the distal end of the debridement tip; and a collection chamber adjacent the proximal end, the collection chamber being an enlargement of the outer cannula such that the collection chamber defines an enlarged portion of the annular suction path.

2. The debridement tip of claim 1 wherein the collection chamber is a frustoconical shape increasing in diameter in the direction of fluid flow.

3. The debridement tip of claim 1 wherein the outer cannula and the collection chamber are flexible so that one of the outer cannula and the collection chamber will at least partially collapse when the outer cannula becomes blocked.

4. The debridement tip of claim 3 wherein one of the outer cannula and the collection chamber is made of a material having a durometer hardness in the range of 5 to 90 Shore A.

5. The debridement tip of claim 1 further comprising a filter located in the suction path near the proximal end such that some of the debris picked up by the outer cannula is stopped by the filter and retained in the collection chamber.

6. A debridement tip having a proximal end and a distal end, the proximal end having connectors for connecting to an irrigation source and a suction source, the tip comprising:

a base adjacent the proximal end, the base containing a fluid port and a suction port, an inner cannula attached to the base in communication with the fluid port and defining a fluid path from the proximal end to the distal end;

an outer cannula surrounding the inner cannula, the outer cannula attached to the base in communication with the suction port and defining an annular suction path from the distal end to the proximal end;

a collection chamber adjacent the proximal end, the collection chamber being an enlargement of the outer cannula such that the collection chamber defines an enlarged portion of the annular suction path; and filter located in the suction path near the proximal end such that some of the debris picked up by the outer cannula is stopped by the filter and retained in the collection chamber, wherein the filter is securely attached to the base and the outer cannula is attached to the base by a snap fit between the base and the collection chamber such that the outer cannula can be detached from the base to allow emptying of the collection chamber.

7. The debridement tip of claim 6 wherein the inner cannula passes through the filter.

8. A debridement tip having a proximal end and a distal end, the proximal end having connectors for connecting to an irrigation source and a suction source, the tip comprising:

a base adjacent the proximal end, the base containing a fluid port and a suction port an inner cannula attached to the base in communication with the fluid port and defining a fluid path from the proximal end to the distal end;

an outer cannula surrounding the inner cannula, the outer cannula attached to the base in communication with the suction port and defining an annular suction path from the distal end to the proximal end;

a collection chamber adjacent the proximal end, the collection chamber being an enlargement of the outer cannula such that the collection chamber defines an enlarged portion of the annular suction path; and a filter located in the suction path near the proximal end such that some of the debris picked up by the outer cannula is stopped by the filter and retained in the collection chamber, wherein the filter comprises a frustoconical projection containing a plurality of filter holes.

9. The debridement tip of claim 8 further comprising a frustoconical post-filter suction chamber enclosed by the filter and the base such that fluid passes through the filter into the post-filter suction chamber, the post-filter suction chamber being in fluid communication with the suction port.

10. A debridement tip having a proximal end and a distal end, the proximal end having connectors for connecting to an irrigation source and a suction source, the tip comprising:

a base adjacent the proximal end, the base containing a fluid port and a suction port, an inner cannula attached to the base in communication with the fluid port and defining a fluid path from the proximal end to the distal end;

an outer cannula surrounding the inner cannula, the outer cannula attached to the base in communication with the suction port and defining an annular suction path from the distal end to the proximal end;

a collection chamber adjacent the proximal end, the collection chamber being an enlargement of the outer cannula such that the collection chamber defines an enlarged portion of the annular suction path; and a filter located in the suction path near the proximal end such that some of the debris picked up by the outer cannula is stopped by the filter and retained in the collection chamber, wherein the outer cannula is collapsible at the distal end.

11. The debridement tip of claim 10 wherein the outer cannula contains a slit to allow the outer cannula to collapse to a smaller diameter.

12. The debridement tip of claim 10 further comprising three longitudinal slits of unequal length to allow the outer cannula to collapse to a smaller diameter.

13. A debridement tip having a proximal end and a distal end, the proximal end having connectors for connecting to an irrigation source and a suction source, the tip comprising:

a base adjacent the proximal end, the base containing a fluid port and a suction port, an inner cannula attached to the base in communication with the fluid port and defining a fluid path from the proximal end to the distal end; and an outer cannula surrounding the inner cannula, the outer cannula attached to the base in communication with the suction port and defining an annular suction path from the distal end to the proximal end, the outer cannula being collapsible at the distal end.

14. The debridement tip of claim 13 wherein the outer cannula contains a slit extending to the distal end, the slit forming segments which can overlap to allow the outer cannula to collapse to a smaller diameter.

15. The debridement tip of claim 13 further comprising three longitudinal slits of unequal length to allow the outer cannula to collapse to a smaller diameter.

* * * * *